United States Patent
Tacito et al.

(10) Patent No.: US 6,533,124 B1
(45) Date of Patent: *Mar. 18, 2003

(54) QUALITY CONTROL SYSTEM FOR MONITORING AND CONTROL OF CONTAMINANTS IN RECYCLED PLASTICS

(75) Inventors: Louis D. Tacito, Merrimack, NH (US); Adam Marciniszyn, Epping, NH (US)

(73) Assignee: Plastics Forming Enterprises, Inc., Manchester, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/514,841

(22) Filed: Feb. 28, 2000

Related U.S. Application Data

(62) Division of application No. 09/136,716, filed on Aug. 19, 1998.

(51) Int. Cl.$^7$ .............................. B07B 13/00; F26B 11/12
(52) U.S. Cl. ........................... 209/3.1; 209/11; 209/913; 34/132; 34/179
(58) Field of Search ........................... 209/3.1, 11, 913; 34/126, 132, 179; 422/89, 91

(56) References Cited

U.S. PATENT DOCUMENTS

| | | | |
|---|---|---|---|
| 4,591,467 A | * 5/1986 | Kopernicky | 264/37.17 |
| 5,108,705 A | 4/1992 | Rounbehler et al. | 422/89 |
| 5,366,091 A | * 11/1994 | Stahl et al. | 209/11 |
| 5,465,503 A | 11/1995 | Oates | 34/179 |
| 5,688,693 A | 11/1997 | Fine et al. | 436/43 |
| 5,733,783 A | 3/1998 | Fine et al. | 436/43 |
| 6,099,659 A | * 8/2000 | Tacito et al. | 134/19 |

FOREIGN PATENT DOCUMENTS

| | | | | |
|---|---|---|---|---|
| JP | 58-148108 | * 9/1983 | | 209/913 |
| WO | WO95/15244 | 6/1995 | | B29B/17/02 |
| WO | WO95/32780 | 12/1995 | | B01B/1/00 |

* cited by examiner

Primary Examiner—Tuan N. Nguyen
(74) Attorney, Agent, or Firm—Grossman, Tucker, Perreault & Pfleger, PLLC

(57) ABSTRACT

An apparatus and process for continuously discriminating between a contaminated plastic material containing trapped volatile contaminants and plastic material which contains an acceptable threshold of contaminants including first supplying a continuous source of plastic material wherein the plastic material contains trapped volatile contaminants and feeding a sample of the plastic material to the input section of an auger conveyor. The auger conveyor contains a barrel and a transfer screw positioned within the barrel with flights thereon for conveying the plastic material, the auger also connected to an output section which itself is connected to a detector for detecting trapped volatile contaminants. Plastic material is then conveyed through the auger at a selected rate by rotation of the transfer screw and the auger is also heated to a selected temperature such that trapped volatile contaminants in the plastic material are removed therefrom and remain substantially within the flights and delivered to the detector. The apparatus and process herein is also configured in active communication with a tracking database containing one or a plurality of programmable logic controllers (PLC's) which signal, divert and/or isolate contaminated recycled material from plastic material which contains an acceptable threshold of contaminants when the recycled material exceeds preselected contamination levels.

3 Claims, 5 Drawing Sheets

US 6,533,124 B1

QUALITY CONTROL SYSTEM FOR MONITORING AND CONTROL OF CONTAMINANTS IN RECYCLED PLASTICS

This application is a division of U.S. Ser. No. 09/136, 716, filed Aug. 19, 1998, now U.S. Pat. No. 6,099,659.

FIELD OF THE INVENTION

This invention relates to a quality control (QC) system for continuous sampling and monitoring of contaminants in recycled plastic materials. More specifically, the present invention relates to a QC system for sampling and determining the presence of certain substances, such as contaminants, within plastic material recycled from polyethylene terepthalate (PET) containers. In further aspect, the QC system herein also uniquely provides for direct in-plant continuous control and detection of contaminants in post-consumer recycled plastic materials thereby expanding post-consumer recycled plastic material markets and applications.

BACKGROUND OF THE INVENTION

Plastic material is now common in everyday life, and ultimately, when used as a disposable product, plastic has also found itself as a significant contributor to the problem of solid waste management. With respect to solid waste management, several different options have been identified to date to deal with the ever increasing need to conserve the valuable and non-renewal resources associated with plastic material production and disposal. For example, "source reduction" which refers to a reduction in the amount of material that is used in any application, and, therefore, a reduction in the amount of material potentially discarded when that use is completed.

However, recycling remains a much more environmentally favored route over "source reduction", and is based upon the reprocessing and refabrication of a plastic material that has been used and discarded by the consumer which otherwise would be destined for disposal. This type of recycling has now become well known as post-consumer recycling (PCR), as opposed to recycling that develops as part of the reuse of by-products from a plastic manufacturing process (which by-products are generally known as "regrind").

Unfortunately, the reprocessing and refabrication of PCR materials into useful products requires several steps (collection, handling/sorting, reclamation/cleaning and end-use fabrication) and presents unique problems. That is, each of these steps has remained relatively expensive, not the least of which is the requirement to insure that the recycled plastic material at issue is clean and safe for consumer reuse. In that regard, it is an altogether simple matter to envision that while in the hands of consumers, intentionally or otherwise, plastic materials can and will come into contact with other more toxic chemicals, and as plastic materials can absorb such toxins, this requires cleaning and detection (of any residual toxins) prior to placement of such material back into the consumer's hands. Of course, this is even more the case to the extent that the recycled material is targeted for an application involving direct food or beverage contact.

Not surprisingly therefore, and to assure consumer safety, regulatory agencies promptly became active with respect to the use of PCR material for food/beverage applications. For example, in 1992 the Food and Drug Administration published proposed guidelines for recycling, which divided plastics recycling into three classes: Primary recycling of plastics which are plant scrap without any consumer exposure; Secondary recycling involving the physical cleaning of post-consumer plastics by physical processes such as washing, vacuum and heat treatment; and Tertiary recycling involving chemical treatment, usually depolymerization (breaking the plastic material down into its building blocks, known as "monomers"), followed by monomer purification and reconstitution back to plastic material. See, "Points to Consider for the Use of Recycled Plastics in Food Packaging: Chemistry Considerations", U.S. FDA, Center for Food Safety and Applied Nutrition (HFS-245), Washington, D.C. April 1992.

With regards to secondary recycling, it should now be apparent that central to any efficient physical cleaning operation is the need to monitor the washing procedures to determine whether or not any recycled plastic material at issue is void of residual contaminant, or whether or not the residual contaminant is present at a level such that it would not migrate out when placed in contact with a food/beverage media. For further discussion see, e.g., "*The Threshold of Regulation and its Application to Indirect Food Additive Contaminants in Recycled Plastics*", Food Additives and Contaminants", 1997, Vol. 14, No. 6–7, 661–670.

Toward such monitoring objectives, a variety of U.S. Patents have been issued directed at sampling and determining the presence of contaminants in recyclable plastic materials, which for the most part have been based upon the well-known analytical tool known as gas chromatographic (GC) instrumentation. Chromatography provides timewise separation of gases or liquid samples as part of analyses in which specific compounds are detected. This timewise separation achieved among constituents permits particular compounds to be distinguished from interferents and from other specific compounds of interest by signal peaks which occur at distinct times at the output of detectors downstream of the chromatograph. The times at which the detector "detects" a given constituent, as well as the amplitude and shape can be predetermined by calibration techniques using samples of known composition, and detection systems containing the chromatographs can be electronically programmed to provide alarms or specific responses upon detection of each compound of interest.

For example, in U.S. Pat. No. 5,073,203, entitled "Method for Recycling Polyethylene Terephthalate (PET) Beverage Bottles by Treating with Carbon Dioxide", there is disclosed a method for recycling polymer materials based on PET used for food packaging such as beverage bottles. As disclosed therein, when such PET resin, in the form of crushed bottles, is washed/extracted by a fluid such as supercritical $CO_2$, at preferred temperatures between 31° and 245° C., the contaminants therein are removed, without any effect on the PET intrinsic viscosity. The washed PET is then tested by GC equipment, and the GC tests therein indicated that under such conditions the contaminant material had been successfully removed.

Attention is also directed to U.S. Pat. Nos. 4,830,192, 4,858,768 and 5,067,616 which describes a method of discriminating between contaminated and uncontaminated containers prior to washing by testing the residue of the container to determine if the residue is the residue of the original product in the container. If the residue is not sufficiently similar to the original product, the container is rejected as contaminated.

Other related disclosures of interest include U.S. Pat. No. 5,108,705, which discloses a method and apparatus for high speed, selective detection of vapors of specific compounds, utilizing a bypass branch and high speed gas chromatography for improved selectivity and detection. In U.S. Pat. No. 4,843,016 a detection system is disclosed for detecting the presence of predetermined compounds in a sample. This system similarly comprises a sample injector, a chromatographic column, a conversion means and one or more specific gas detectors. The conversion means is said to transform the column effluent to combustion products in the gas phase, after which those combustion products are transferred to the specific gas detectors.

In U.S. Pat. No. 4,880,120, entitled "Plastic Container Inspection Process", there is disclosed a container inspection process for detecting the presence of contaminants in plastic containers. More specifically, the process flushes volatiles from within the container by injecting gas, draws a vapor sample from within the container and analyzes the sample by ionization techniques.

In U.S. Pat. No. 5,352,611 there is disclosed a method and apparatus for samples and determining the presence of residues of contaminants in containers. The method includes the steps of injecting a fluid described as air or $CO_2$ into the containers in order to displace a portion of the contents, evacuating a sample of the container contents so displaced by applying suction thereto, and analyzing the sample evacuated to determine the presence or absence of any residues therein.

Accordingly, while various efforts have been made for monitoring contaminants in recycled material, as the above discussion has shown, many of these techniques in one form or another focus on the sampling of contaminant from an individual contaminated container, which is an uncooperative requirement as applied to the goal of developing a fast and efficient recycling operation with continuous output. That is, sampling each and every individual container collected and ultimately reprocessed through a recycling facility is time-consuming and economically unattractive, particularly as the need for high-speed recycling grows in the marketplace.

Furthermore, in the case of previous attempts to monitor contaminants in recycled ground flake, as opposed to the container itself in a given recycling facility, to date there have been no reports wherein such procedure is efficiently coordinated with an in-plant continuous method for discriminating between levels of contamination derived from a given population of, e.g. PET containers. In other words, to the extent that PCR-PET flake has been analyzed for contaminants, it has been largely demonstrated on isolated portions of the flake, and not itself coupled to an in-plant continuous quality control system to satisfy, e.g., the strict requirements discussed above set by the FDA for the preparation of food grade packages made from recycled material.

Stated another way, none of the techniques disclosed to date have developed a method to continuously trigger a more reliable concentration of contaminants per unit of air space (above contaminated flake material) which in turn would provide far greater and more reliable detection capability. And towards such end, the prior art has also yet to develop a technique whereby one ensures that ejected volatile contaminant gases remain substantially within the air spaces between a relatively large sample of flake so that such contaminants can themselves be delivered to a detection station removed from that location where the contaminant gases are first made to migrate out of a given sample.

Furthermore, none of the prior art disclosures to date have coordinated and assimilated detection information/data into a tracking data management center which is configured in active communication and coordinates control of a recycling plant's processing of recycled material such that said tracking data management center can signal, divert and/or isolate contaminated recycled material from non-contaminated material when said recycled material exceeds preselected contamination levels. Nor has the prior art recognized the utility and advantage of coordinating the monitoring and control of contaminated flake to the extent that such monitoring and control is applied both to incoming and so-called "dirty" flake, and to flake that has been processed (i.e., "cleaned") through a recycling plant facility.

Therefore, it is a primary object of the present invention to provide a method and system for the monitoring and control of contaminants in a specific portion of the production of shredded, pelletized or flaked plastic materials. More specifically it is a primary object of the present invention to continuously monitor and detect the presence of trapped volatile contaminant substances in a recycled plastic material as the recycled material is selectively sampled from a main recycling production line facility, to deliver such monitoring information to a programmable logic controller (PLC) which is programmed to both identify and signal at a preselected contaminant levels, as well as acting to divert and isolate PCR plastic containing said selected and detected contaminant level from plastic material which contains an acceptable threshold of contaminants.

Accordingly, it is an object of the present invention to provide a unique and overall QC system for continuous sampling, monitoring and detection of contaminants in recycled plastic materials, including both dirty and clean flake, and to coordinate such system directly with in-plant process control, wherein the recycled plastic material is specifically recycled PET.

SUMMARY OF THE INVENTION

A process for continuously discriminating between a contaminated plastic material containing trapped volatile contaminants and plastic material which contains an acceptable threshold level of contaminant in a recycling plant wherein said plant is reprocessing recycled plastic material comprising the steps of first supplying a continuous source of plastic material wherein said plastic material contains trapped volatile contaminants and feeding a sample of said continuous source of plastic material to detector apparatus wherein said detector apparatus comprises a chamber which chamber regulates the temperature of said plastic material in said chamber. One then regulates the temperature of said plastic material in said chamber so that said trapped volatile contaminants in said plastic material are partially or completely removed from said plastic material and detecting said removed volatile contaminants with said detector apparatus to determine the presence or absence of contaminants in said plastic material wherein said detector apparatus communicates said detected levels of contaminants to a tracking database wherein said tracking database is configured in communication with said detector and further controls said recycling plant's reprocessing of recycled material such that said tracking database can signal, divert and/or isolate said contaminated recycled material from plastic material which contains an acceptable threshold of contaminant when said recycled material exceeds preselected contamination levels.

In apparatus form the present invention comprises an apparatus for continuously discriminating between a contaminated plastic material containing trapped volatile contaminants and plastic material which contains an acceptable threshold of contaminants, comprising an auger conveyor wherein said auger conveyor comprises an input hopper and a barrel containing heating elements and a transfer screw with flights thereon, positioned within said barrel, said flights for conveying said plastic material, wherein said auger further contains an output section connected to a volatile gas detector for detecting said trapped volatile contaminants.

DETAILED DESCRIPTION OF THE INVENTION

Figure 1:
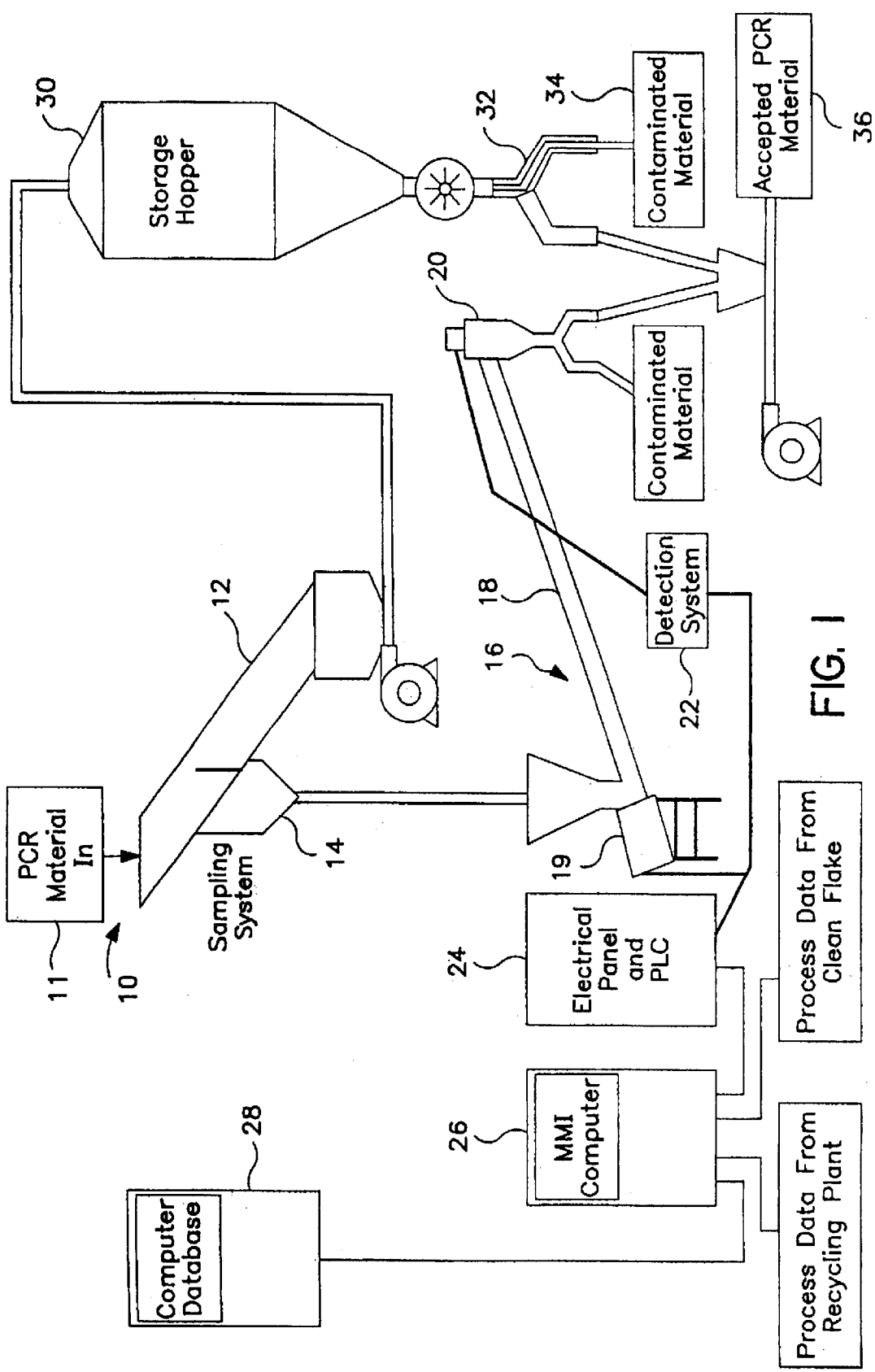
FIG. 1 is a schematic block diagram of a basic apparatus lay-out of the invention herein for detection of volatile contaminants in sampled recycled plastic from a main recycling production line facility as combined with a PLC tracking database controller for signaling and diverting PCR plastic at selected threshold contaminant levels from non-contaminated PCR plastic.

As illustrated in FIG. 1, shown is an input section 10 wherein PCR material is continuously delivered to a conveyor 12 which contains a sampling system 14 for diverting a sample of said continuous source of PCR to detector apparatus 16. In preferred embodiment, detector apparatus comprises an auger conveyor 18 which contains a barrel and a transfer screw (not shown), the transfer screw rotated by machine 19 wherein said auger includes an output section 20. The output section 20 is connected to a detector system 22, preferably via a ¼ inch open tube for transfer of volatile gases, which detector is in active communication with tracking database 24.

The auger conveyor 18 preferably contains one or a plurality of heating zones which can be regulated to a desired temperature. The heating zones can be incorporated directly within said auger barrel, and preferably, 3 or 4 zones have been found satisfactory. With regard to temperature control, the zone temperatures are set such that the temperature will be sufficient to drive trapped volatiles from the dirty PCR PET plastic, but not so high such that other material present in the flake (e.g., glue, or other lower melting polymers such as polyethylene) will cause sticking or melting. In that regard, it has been found preferable to adjust the barrel temperature zones of the auger to about 300° F., e.g. between about 275° F.–325° F., which in practice has been found to effect a temperature of about 160–210° F. in the PET flake itself. However, clean flake is preferably sent through the auger with an average barrel temperature of about 350–475° F., which in turn will heat the clean PET flake to about 200–450° F. With respect to clean flake, therefore, the plastic should be heated again to a temperature that drives off volatiles, but not so high that the plastic will stick or melt together. Furthermore, whether with clean or dirty flake, it will be appreciated that whatever amounts to the selected barrel or flake temperature, such temperature is obtained at a selected heating rate.

In accordance with the present invention, the auger conveyor can be horizontal, or preferably set at an angle, as shown in FIG. 1, wherein said angle is preferably set between 1–90 degrees, and more preferably, about 5–40 degrees, as well as between 10–30 degrees, and in a most preferred embodiment, the angle is between about 15–25 degrees. By adjusting the angle of the auger 18 such is observed to increase the amount of material in the barrel (i.e., more material per flight of the screw therein) as well as the residence time of the material in the barrel, thereby providing more sample per unit section of the barrel for eventual detection. In addition, preferably, the auger barrel inner diameter is about 2.0 to 10.0 inches and said transfer screw has an inner diameter of about 2.0 to 10.0 inches. In addition, preferably, the auger barrel is of length of about 10 to 30 feet, and the plastic material remains within said auger for a time of about 2.0 minutes, and more preferably, for a time between 2.0–10.0 minutes.

Also illustrated in FIG. 1 and in communication with the tracking database and programmable logic controller 24 is computer device 26 containing a machine/man interface screen (or "MMI") which itself is in communication with computer database 28, and as illustrated, units 24, 26 and 28 are all connected to one another in accordance with the in-plant quality control system of the present invention. More specifically, computer 28 is in active communication with computer device 26 which is in receipt of process data from the recycling plant, such as critical control parameters. These include the following: sorting of the recycled material (e.g., separating non-PET polymers, separation by color, separation of metal or other waste from the plastic); grinding (e.g., monitor of grinding power and gravity separation of light materials, such as labels and other lightweight fine material); chemical composition of the wash solution; temperature control of the wash process or various washing processes; wash water recovery systems (e.g. monitoring of wash water purity); density separation; rinsing control (e.g., temperature of rinse and flow rate); and dryer control (e.g., temperature regulation). In addition, computer device 26 is in receipt of process data from clean flake, i.e., the invention herein as applied to sampling and monitoring the contaminants in recycled and cleaned plastic flake material. See FIG. 2.

Finally, with respect to FIG. 1, as also illustrated therein, conveyor 12 conveying incoming dirty flake material delivers such dirty flake material to storage hopper 30 which hopper contains a diversion mechanism 32 for diverting/separating contaminated material 34. In addition, diversion mechanism 32 is in communication with controller 24 (not shown) such that when detection system 22 identifies a level of volatile contaminant at 20 that exceeds a preselected threshold level, diversion mechanism 32 is instructed to divert and separate such material from any farther in-plant reprocessing and conversion to clean flake. Finally, as seen in FIG. 1, that material which does not indicate volatile contaminant levels below a preselected level (input at 26) is identified in FIG. 1 as "Accepted PCR" 36 for processing/cleaning into recycled "clean" flake.

Figure 2:
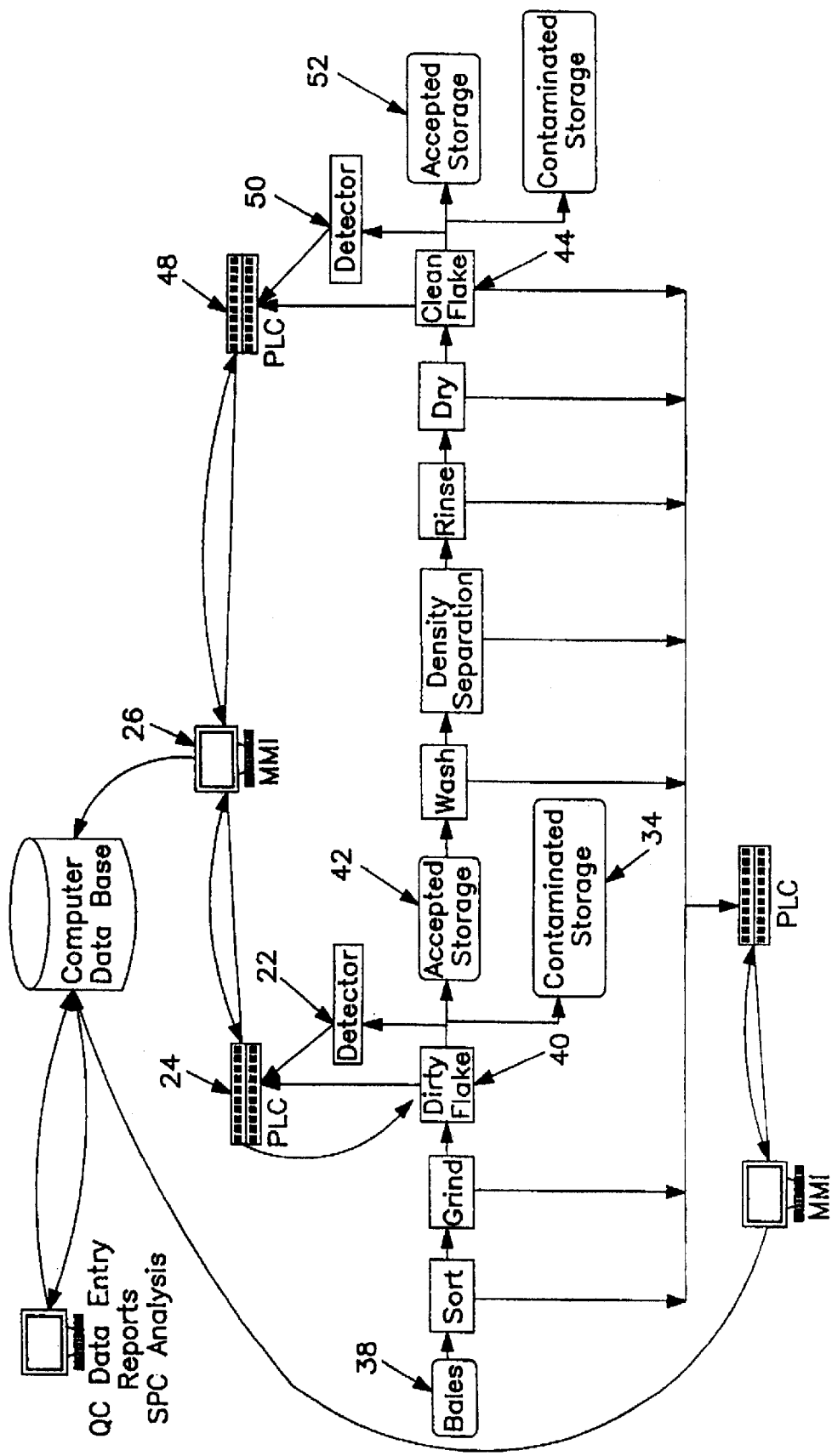
FIG. 2 is a block diagram flow-sheet further illustrating the invention herein as configured to simultaneously evaluate both unclean and cleaned PCR plastic material.
Figure 3A:
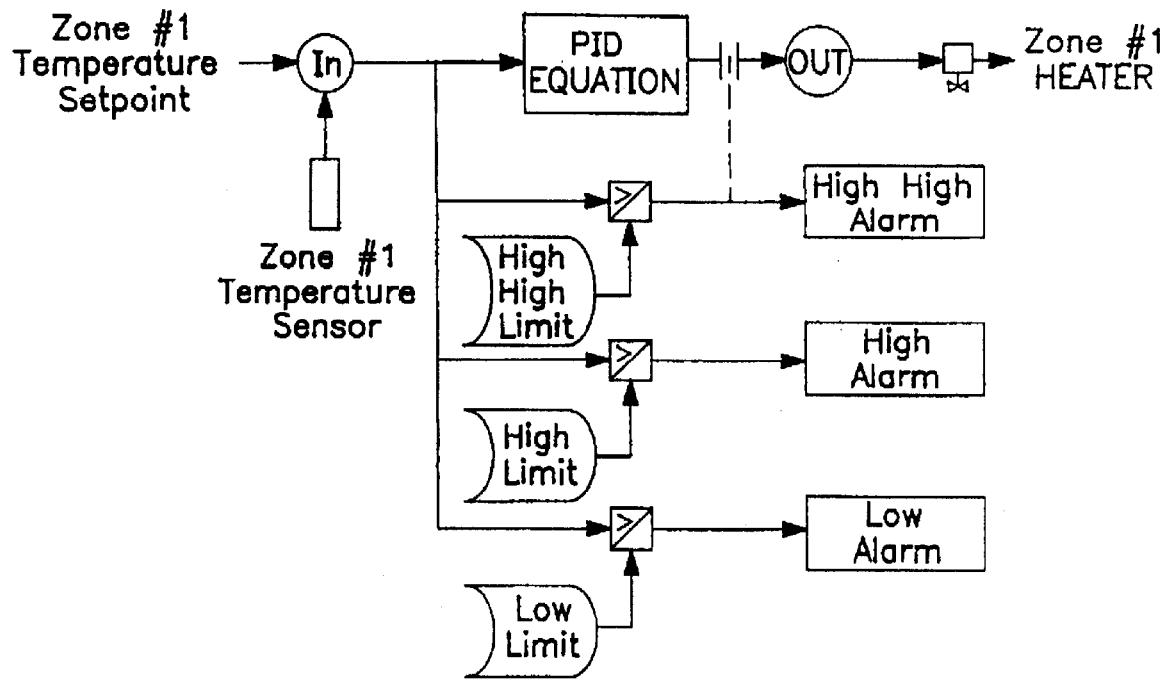
FIGS. 3A, 3B, 3C, 3D and 3E are additional block diagrams identifying the PLC controller input variables and associated controller command options.
Figure 3B:
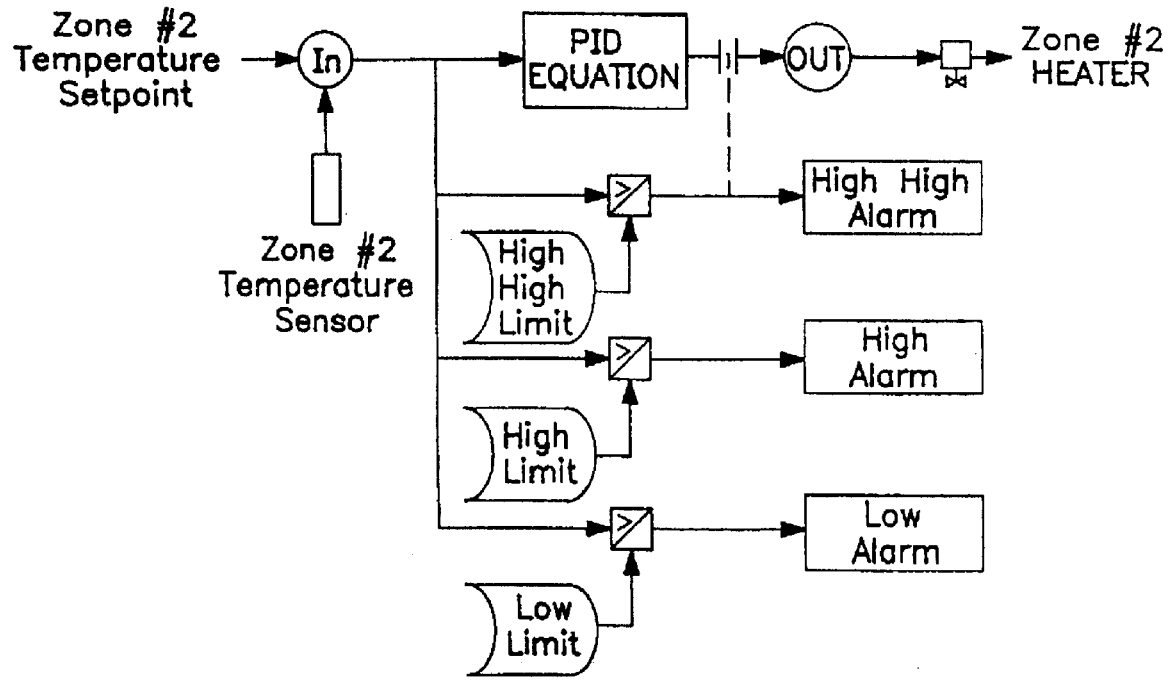
Figure 3C:
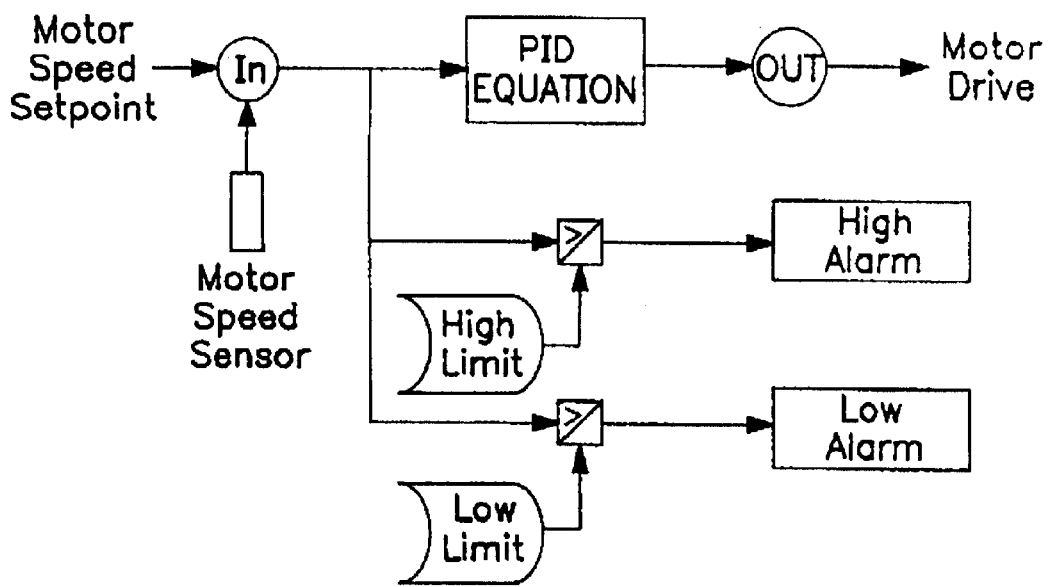
Figure 3D:
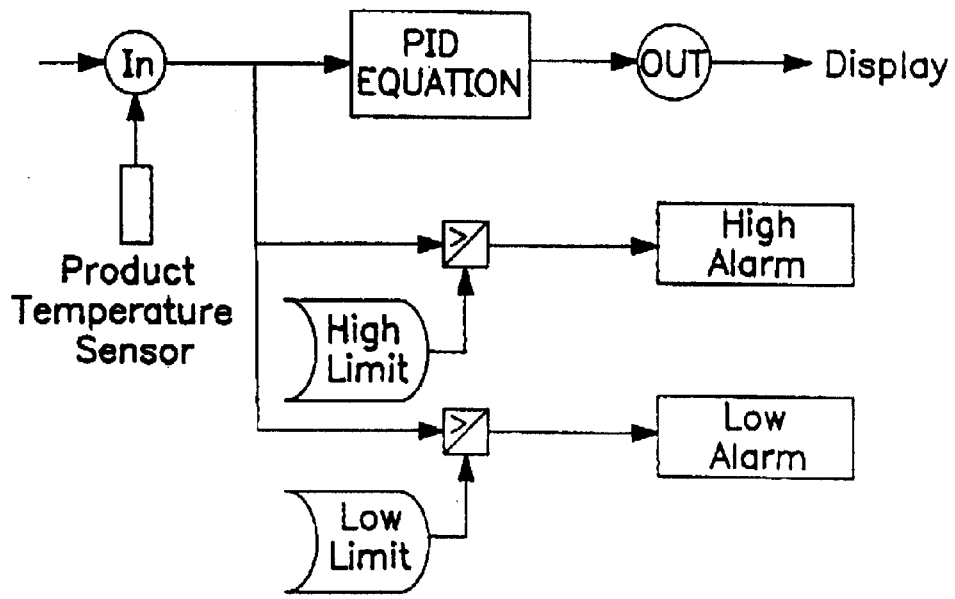
Figure 3E:
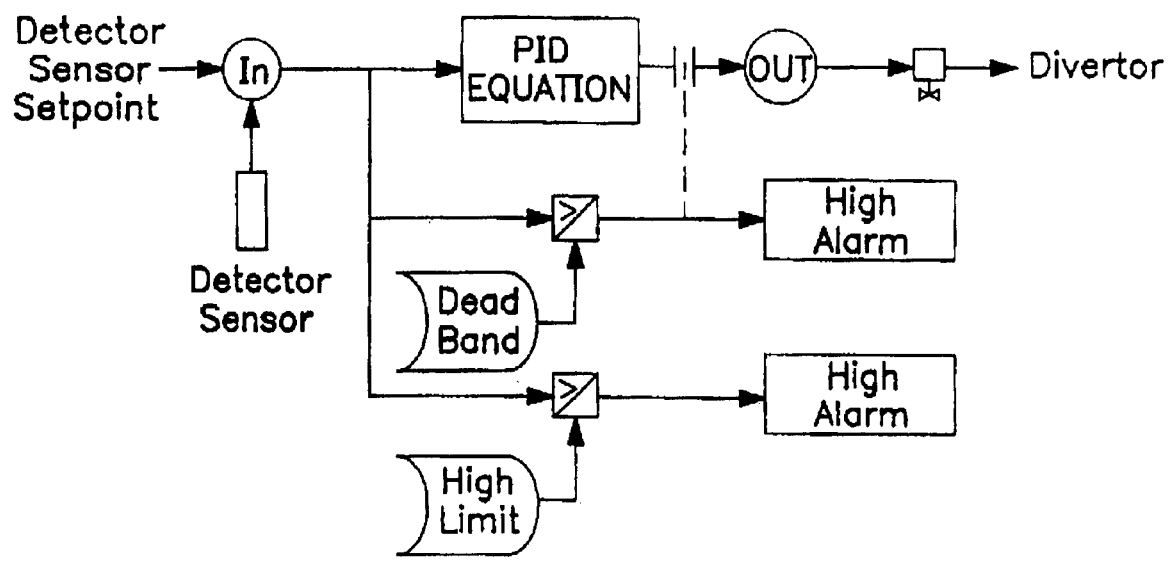

Attention is next directed to FIG. 2, which as noted, is a block diagram flowsheet further illustrating the invention herein as configured to simultaneously evaluate both unclean and cleaned PCR plastic material. That is, bales of plastic for recycling are shown as entering the recycling facility at 38 followed by sorting and grinding and then at 40, being sampled in accordance with the illustration shown in FIG. 1. Accordingly, the accepted PCR material is stored at 42 followed by washing, a density separation treatment preferably accomplished by a sink/float or hydroclone treatment to separate out, by density, those materials with a density of about 1.0 g/cc, followed by a rinse step, and drying. Then, at 44, such "clean" flake is again sampled through the system of FIG. 1, thereby providing an additional QC sampling and monitoring of the "clean" flake material (an additional PLC is shown at 48 in communication with detector 50) to assure that material ultimately delivered at 52 does not contain volatile contaminants, again, at or above a preselected contaminant level selected and input to the PLC controller at 24. Detector 22 and 50 are commercially available and known as continuous flame ionization detectors (FID) or one can employ photoionization detection instrumentation.

FIGS. 3A, 3B, 3C, 3D and 3E identify the control loops required to maintain process control which facilitate obtaining the proper relationship between the sensor and sampling device. In addition, each individual control loop is further contained in a control alogarithm which executes the specific ladder logic for the statistical process control of the present invention. In addition, the control alogarithm sends the information to the MMI computer 26 which presents the information to an operator and also forwards the information automatically to computer database 28.

This invention has been described in terms of specific embodiments set forth above, but it should be understood that these are by way of illustration only and the the invention is not necessarily limited thereto. Modifications and variations will be apparent from this disclosure and may be resorted to without departing from the scope of this invention. Accordingly, such variations and modifications of the invention are considered to be within the purview of this invention and the following claims.

What is claimed is:

1. An apparatus for continuously discriminating between a plastic material containing-trapped volatiles and plastic material which contains an acceptable threshold of volatiles, comprising a detector apparatus wherein said detector apparatus comprises a chamber which chamber regulates the temperature of said plastic material in said chamber so that said trapped volatiles in said plastic material are removed from said plastic;

a computer tracking database in communication with said detector apparatus, wherein said tracking database can signal, divert and/or isolate plastic material containing trapped volatiles from plastic material which contains an acceptable threshold of volatiles when said plastic material containing trapped volatiles exceeds preselected volatile levels.

2. An apparatus for continuously discriminating between a plastic material containing trapped volatile contaminants and plastic material without trapped volatiles comprising an auger conveyor wherein said auger conveyor comprises an input hopper and a barrel containing heating elements and a transfer screw with flights thereon positioned within said barrel, said flights for conveying said plastic material, wherein said auger further contains an output section connected to a volatile gas detector for detecting said trapped contaminants wherein said detector is connected to an electronic tracking database containing stored signal responses representative of said volatiles at selected concentrations, wherein said detector is able to generate a signal response characteristic of said volatile contaminant concentration and said tracking database compares said detector signal response to said stored signal responses, and wherein said tracking database identifies said plastic material containing trapped volatiles when said detector signal response meets or exceeds stored signal responses in said tracking database.

3. The apparatus of claim 2 wherein said auger is angled as between said input and output section so that said input and output sections are not horizontally disposed to one another.

* * * * *